United States Patent

Docherty et al.

[11] Patent Number: 5,883,241
[45] Date of Patent: Mar. 16, 1999

[54] DNA SEQUENCES CODING FOR A HUMAN METALLOPROTEINASE AND VARIANTS THEREOF

[75] Inventors: Andrew James Penrose Docherty, Guildford; Patrick Marcel Slocombe, Bracknell, both of United Kingdom

[73] Assignee: Celltech Therapeutics Limited, Berkshire, United Kingdom

[21] Appl. No.: 836,443

[22] PCT Filed: Sep. 5, 1996

[86] PCT No.: PCT/GB96/02180

§ 371 Date: Jun. 24, 1997

§ 102(e) Date: Jun. 24, 1997

[87] PCT Pub. No.: WO97/09420

PCT Pub. Date: Mar. 13, 1997

[30] Foreign Application Priority Data

| Sep. 5, 1995 | [GB] | United Kingdom | 9518026 |
| Oct. 20, 1995 | [GB] | United Kingdom | 9521496 |
| Oct. 20, 1995 | [GB] | United Kingdom | 9521497 |
| Dec. 21, 1995 | [GB] | United Kingdom | 9526230 |
| Jun. 11, 1996 | [GB] | United Kingdom | 9612145 |

[51] Int. Cl.$^6$ .................................................. C12N 15/57
[52] U.S. Cl. ....................... 536/23.2; 435/212; 435/226
[58] Field of Search ........................... 536/23.2; 435/212, 435/226

[56] References Cited

FOREIGN PATENT DOCUMENTS

WO 87/07907  12/1987  WIPO .
WO 90/10062   9/1990  WIPO .
WO 92/09701   6/1992  WIPO .
WO 95/06031   3/1995  WIPO .

OTHER PUBLICATIONS

L. Matrisian, TIG, Apr. 1990 vol. 6, No. 4, pp. 121–125.
T. Yagami–Hiromasa, et al., Nature, vol. 377, pp. 652–656 (Oct. 19, 1995).
Weskamp, et al., J. of Cell Biol., vol. 132, No. 4, 717–725 (1996).
Chander, et al. J. Phamac. Sci vol. 84, No. 4, 404–409 (1995).
Will, et al., J. of Biol. Chem., vol. 271, No. 29, 17119–17123 (1996).
Crabbe, et al., Biochemistry 33, 14419–14425 (1994).
Murphy, et al., J. of Bio. Chem., vol. 267, No. 14, 9612–9618 (1992).
Edamatsu, et al., J. Biochem, vol. 112, No. 5, 637–642 (1992).
Feehan, et al., J. Biochem., vol. 271, No. 12, 7019–7024 (1996).
Walcheck, et al., Nature, vol. 380 720–723 (1996).
Lasky, Science, vol. 258, 964–969 (1992).
Mohler, et al., Nature, vol. 370, 218–220 (1994).
Gearing, et al., Nature, vol. 370, 555–561 (1994).
McGeehan, et al., Nature, vol. 370, 558–561 (1994).
Kratschmar, et al., J. Biochem., vol. 271, No. 9, 4593–4596 (1996).
Yoshida, et al. Int. Immunol. 2(6), 585–591 (1990).

*Primary Examiner*—Charles L. Patterson, Jr.
*Attorney, Agent, or Firm*—David G. Conlin; David S. Resnick; Dike, Bronstein, Roberts, & Cushman, LLP

[57] ABSTRACT

DNA sequences coding for a human metalloproteinase are described together with the corresponding antisense DNA and RNA. The DNA may be used to produce the metalloproteinase which may be used to generate antibodies thereto and to obtain other compounds capable of regulating the action of the metalloproteinase in vivo.

4 Claims, No Drawings

DNA SEQUENCES CODING FOR A HUMAN METALLOPROTEINASE AND VARIANTS THEREOF

This invention relates to a novel human metalloproteinase, to homologues and fragments thereof, to means for producing the metalloproteinases, and to means for regulating their production and activity in vivo.

A number of physiologically important processing events are mediated by metalloproteinases, which under certain circumstances contribute to pathologies as diverse as inflammation and cancer, and it has been suggested that such enzymes would provide targets for therapeutic intervention. Thus, by varying the production of the enzyme, or inhibiting or enhancing its activity in vivo it should be possible to achieve a therapeutic effect.

In one example, tumour necrosis factor-alpha (TNF-α) is a potent pro-inflammatory and immunomodulatory mammalian cytokine produced primarily by activated monocytes and macrophages. It is initially expressed as a 233-amino-acid membrane-anchored precursor (pro-TNF-α) which is proteolytically processed to yield the mature, 157-amino-acid cytokine. Evidence has been obtained which indicates that at least one metalloproteinase-like enzyme mediates pro-TNF-α cleavage, but to date the enzyme(s) responsible for this in vivo are unknown [see for example Mohler, K. M. etal, Nature 370, 218–220 (1994); Gearing, A. J. et al ibid 370, 555–557 (1994); McGeehan, G. M. et al, ibid 370, 558–561 (1994)]. A number of known matrix metalloproteinase inhibitors have been shown to block TNF-α secretion [see the above papers and International Patent Specification Publication No. WO 95/06031]. These compounds were originally designed to selectively inhibit matrix metalloproteinases such as collagenase with primary functions unrelated to pro-TNF-α cleavage. Where new inhibitors have been described these have apparently been selected on the basis of their effect on TNF-α secretion seen in cell-based assays.

In another example, L-selectin shedding is thought to be a pro-inflammatory event that is mediated by an as yet unidentified metalloproteinase [Lasky, Science, 258, 964–969 (1992)]. Some inhibitors of L-selectin proteolysis have been identified, but these have been obtained using cell based assays [Walchech et al., Nature, 380, 720–723 (1996); Feehan et al., J. Biol. Chem., 271, 7019–7024 (1996)].

In general, in order to obtain compounds capable of selectively regulating the action of a metalloproteinase implicated in human disease, for example as in the above TNF-α and L-selectin instances it would be clearly advantageous to have the enzyme unequivocally identified and obtainable in an isolated, purified and unambiguous characterised form.

Through the use of a cloning and screening approach, we have been able to identify human DNA which is responsible for coding part of one such metalloproteinase. This DNA has the sequence described in SEQ I.D. No: 1 below and may be of use (1) in the generation of a gene coding for the metalloproteinase, (2) in the production of the metalloproteinase, (3) in the provision of means to regulate the activity of the metalloproteinase in vivo, and (4) in the provision of means to detect and measure a metalloproteinase in a biological system, e.g. in serum, synovial fluid or a tissue extract.

Thus according to one aspect of the invention we provide DNA comprising the nucleotide sequence of SEQ I.D. No: 1:

SEQ I.D. No: 1

```
GGTTCGAGCACTCCAAGCCCACACAGGGACTGGGCTCTTCAGTTT
ACCAACAGACCAAGAAGCGACCTCGCAGGATGAAAAGGGAAGATTT
AAACTCCATGAAGTATGTGGAGCTTTACCTCGTGGCTGATTATTTAGA
GTTTCAGAAGAATCGACGAGACCAGGACGCCACCAAACACAAGCTCA
TAGAGATCGCCAACTATGTTGATAAGTTTTACCGATCCTTGAACATCC
GGATTGCTCTCGTGGGCTTGGAAGTGTGGACCCACGGAACATGTG
TGAAGTTTCAGAGAATCCATATTCTACCCTCTGGTCCTTTCTCAGTTG
GAGGCGCAAGCTGCTTGCCCAGAAGTACCATGACAACGCCCAATTAA
TCACGGGCATGTCCTTCCACGGCACCACCATCGGCCTGGCCCCCCT
CATGGCCATGTGCTCTGTGTACCAGTCTGGAGGAGTCAACATGGACC
ACTCCGAGAATGCCATTGGCGTGGCTGCCACCATGGCCCACGAGAT
GGGCCACAACTTTGGCATGACCCATGATTCTGCAGATTGCTGCTCGG
CCAGTGCGGCTGATGGTGGGTGCATCATCATGGCAGCTGCCACTGGGCA
CCCCTTTCCCAAAGTGTTCAATGGATGCAACAGGAGGGAGCTGGACA
GGTATCTGCAGTCAGGTGGTGGAATGTGTCTCCAACATGCCAGAC
ACCAGGATGTTGTATGGAGGCCGGAGGTGTGGGAACGGGTATCTGG
AAGATGGGGAAGAGTGTGACTGTGGAGAAGAAGAGGAATGTAACAA
CCCCTGCTGCAATGCCTCTAATTGTACCCTGAGGCCGGGGGCGGAG
TGTGCTCACGGCTCCTGCTGCCACCAGTGTAAGCTGTTGGCTCCTGG
GACCCTGTGCCGCGAGCAGGCCAGGCAGTGTGACCTCCCGGAGTTC
TGTACGGGCAAGTCTCCCCACTGCCCTACCAACTTCTACCAGATGGA
TGGTACCCCCTGTGAGGGCGGCCAGGCCTACTGCTACAACGGCATG
TGCCTCACCTACCAGGAGCAGTGCCAGCAGCTGTGGGGACCCGGAG
CCCGACCTGCCCCTGACCTCTGCTTCGAGAAGGTGAATGTGGCAGG
AGACACCTTTGGAAACTGTGGAAAGGACATGAATGGTGAACACAGGA
AGTGCAACATGAGAGATGCGAAGTGTGGGAAGATCCAGTGTGTCAGAG
CTCTGAGGCCCGGCCCCTGGAGTCCAACGCGGTGCCCATTGACACC
ACTATCATCATGAATGGGAGGCAGATCCAGTGCCGGGGCACCCACG
TCTACCGAGGTCCTGAGGAGGAGGGTGACATGCTGGACCCAGGGCT
GGTGATGACTGGAACCAAGTGTGGCTACAACCATATTTGCTTTGAGG
GGCAGTGCAGGAACACCTCCTTCTTTGAAACTGAAGGCTGTGGGAAG
AAGTGCAATGGCCATGGGGTCTGTAACAACAACCAGAACTGCCACTG
CCTGCCGGGCTGGGCCCCGCCCTTCTGCAACACCGGGCCACGG
GGGCAGTATCGACAGTGGGCCTATGCCCCCTGAGAGTGTGGGTCCT
GTGGTAGCTGGAGTGTTGGTGGCCATCTTGGTGCTGGCGGTCCTCA
TGCTGATGTACTACTGCTGCAGACAGAACAACAAACTAGGCCAACTC
AAGCCCTCAGCTCTCCCTTCCAAGCTGAGGCAACAGTTCAGTTGTCC
```

-continued

SEQ I.D. No: 1

```
CTTCAGGGTTTCTCAGAACAGCGGGACTGGTCATGCCAACCCAACTT
TCAAGCTGCAGACGCCCCAGGGCAAGCGAAAGGTGTTCCTTGACTT
GTGCGTACAGGTGATCAACACTCCGGAAATCCTGCGGAAGCCCTCC
CAGCCTCCTCCCCGGCCCCCTCCAGATTATCTGCGTGGTGGGTCCC
CACCTGCACCACTGCCAGCTCACCTGAGCAGGGCTGCTAGGAACTC
CCCAGGGCCGGGTCTCAAATAGAGAGGACGGAGTCGTCCAGGAG
GCCTCCTCCAAGCCGGCCAATTCCCCCCGCACCAAATTGCATCGTTT
CCCAGGACTTCTCCAGGCCTCGGCCGCCCCAGAAGGCACTCCCGGC
AAACCCAGTGCCAGGCCGCAGGAGCCTCCCCAGGCCAGGAGGTGC
ATCCCCACTGCGGCCCCCTGGTGCTGGCCCTCAGCAGTCCCGGCCT
CTGGCAGCACTTGCCCCAAAGAGGGTATGGAAGACTTGCAATTTGAA
AACTGGGGACCAGTTCCAAAGTCAGTAATTGTGTTAACCACGTGTATA
ACAGCTCTGCTGGACACCCAAGAAAGCCATGGGAACGCCAACTGGA
AAGGTCCCCTTCCCCAGGGGAGCCTGCGAAGGAGAGGTTCTGTAGA
ATCCAAGCCCACATTTCCAAAGTCACCCCCAACGCGTCCTCTCACAC
CGTCCACTGTGCGTTTGTATGTGTCTGGGATCCAGGGCAATGTGAAT
TTTCTTTTTATTTGGGAGATTGTTCACGGAAAACAGATCTTCTTCTCTC
TTGTCCACCTATTAATTGTTTACAATATTTGTACATCTATGCAAAATAC
TTGAATGGGCCATGGTGCCTTTTTTCCTTGTTAGTATTTAATTAAAAAT
GAATTGTTTGTCATTTGCAAAAAAAAAAAAAAAAAAAA
``` and homologues and fragments thereof.

It will be appreciated that the nucleotide sequence of SEQ I.D. No: 1 also includes control sequences, such as a polyadenylation sequence, providing for expression of the sequence in a host cell.

One particular DNA fragment according to the invention is the isolated human metalloproteinase-encoding nucleotide sequence of SEQ I.D. No: 2:

SEQ I.D. No: 2

```
TTCGAGCACTCCAAGCCCACCACCAGGGACTGGGCTCTTCAGTTTAC
ACAACAGACCAAGAAGCGACCTCGCAGGATGAAAAGGGAAGATTTAA
ACTCCATGAAGTATGTGGAGCTTTACCTCGTGGCTGATTATTTAGAGT
TTCAGAAGAATCGACGAGACCAGGACGCCACCAAACACAAGCTCATA
GAGATCGCCAACTATGTTGATAAGTTTTACCGATCCTTGAACATCCGG
ATTGCTCTCGTGGGCTTGGAAGTGTGGACCCACGGGAACATGTGTG
AAGTTTCAGAGAATCCATATTCTACCCTCTGGTCCTTTCTCAGTTGGA
GGCGCAAGCTGCTTGCCCAGAAGTACCATGACAACGCCCAATTAATC
ACGGGCATGTCCTTCCACGGCACCACCATCGGCCTGGCCCCCCTCA
TGGCCATGTGCTCTGTGTACCAGTCTGGAGGAGTCAACATGGACCAC
TCCGAGAATGCCATTGGCGTGGCTGCCACCATGGCCCACGAGATGG
GCCACAACTTTGGCATGACCCATGATTCTGCAGATTGCTGCTCGGCC
AGTGCGGCTGATGGTGGGTGCATCATGGCAGCTGCCACTGGGCACC
CCTTTCCCAAAGTGTTCAATGGATGCAACAGGAGGGAGCTGGACAG
GTATCTGCAGTCAGGTGGTGGAATGTGTCTCCAACATGCCAGACA
CCAGGATGTTGTATGGAGGCCGGAGGTGTGGGAACGGGTATCTGGA
AGATGGGGAAGAGTGTGACTGTGGAGAAGAAGAGGAATGTAACAAC
CCCTGCTGCAATGCCTCTAATTGTACCCTGAGGCCGGGGCGGAGT
GTGCTCACGGCTCCTGCTGCCACCAGTGTAAGCTGTTGGCTCCTGG
GACCCTGTGCCGCGAGCAGGCCAGGCAGTGTGACCTCCCGGAGTTC
TGTACGGGCAAGTCTCCCCACTGCCCTACCAACTTCTACCAGATGGA
TGGTACCCCCTGTGAGGGCGGCCAGGCCTACTGCTACAACGGCATG
TGCCTCACCTACCAGGAGCAGTGCCAGCAGCTGTGGGGACCCGGAG
CCCGACCTGCCCCTGACCTCTGCTTCGAGAAGGTGAATGTGGCAGG
GACACCTTTGGAAACTGTGGAAAGGACATGAATGGTGAACACAGGAA
GTGCAACATGAGAGATGCGAAGTGTGGGAAGATCCAGTGTCAGAGC
TCTGAGGCCCGGCCCCTGGAGTCCAACGCGGTGCCCATTGACACCA
CTATCATCATGAATGGGAGGCAGATCCAGTGCCGGGGCACCCACGT
CTACCGAGGTCCTGAGGAGGAGGGTGACATGCTGGACCCAGGGCTG
GTGATGACTGGAACCAAGTGTGGCTACAACCATATTTGCTTTGAGGG
CAGTGCAGGAACACCTCCTTCTTTGAAACTGAAGGCTGTGGGAAGAA
GTGCAATGGCCATGGGGTCTGTAACAACAACCAGAACTGCCACTGCC
TGCCGGGCTGGGCCCCGCCCTTCTGCAACACACCGGGCCACGGGG
GCAGTATCGACAGTGGGCCTATGCCCCCTGAGAGTGTGGGTCCTGT
GGTAGCTGGAGTGTTGGTGGCCATCTTGGTGCTGGCGGTCCTCATG
CTGATGTACTACTGCTGCAGACAGAACAACAAACTAGGCCAACTCAA
GCCCTCAGCTCTCCCTTCCAAGCTGAGGCAACAGTTCAGTTGTCCCT
TCAGGGTTTCTCAGAACAGCGGGACTGGTCATGCCAACCCAACTTTC
AAGCTGCAGACGCCCCAGGGCAAGCGAAAGGTGTTCCTTGACTTGT
GCGTACAGGTGATCAACACTCCGGAAATCCTGCGGAAGCCCTCCCA
GCCTCCTCCCCGGCCCCCTCCAGATTATCTGCGTGGTGGGTCCCCA
CCTGCACCACTGCCAGCTCACCTGAGCAGGGCTGCTAGGAACTCCC
CAGGGCCGGGTCTCAAATAGAGAGGACGGAGTCGTCCAGGAGGC
CTCCTCCAAGCCGGCCAATTCCCCCCGCACCAAATTGCATCGTTTCC
CAGGACTTCTCCAGGCCTCGGCCGCCCCAGAAGGCACTCCCGGCAA
```

-continued

SEQ I.D. No: 2

ACCCAGTGCCAGGCCGCAGGACCTCCCCAGGCCAGGAGGTGCAT
CCCCACTGCGGCCCCCTGGTGCTGGCCCTCAGCAGTCCCGGCCTCT
GGCAGCACTTGCCCCAAAGAGGGTATGGAAGACTTGCAATTTGAAAA
CTGGGGACCAGTTCCAGTTCCAAAGTCAG and homologues and fragments thereof.

In the sequences herein standard one letter codes are used to represent nucleotides or amino acids as appropriate.

DNA according to the invention may be obtained using conventional molecular biology procedures, for example by probing a human genomic or cDNA library with one or more labelled oligonucleotide probes containing for example fifteen or more contiguous nucleotides designed using the nucleotide sequences described herein [see for example "Current Protocols in Molecular Biology", Ausubel, F. M. et al (eds), Greene Publishing Associates and Wiley-Interscience, New York (1987)].

Where the term homologue is used herein in relation to a particular nucleotide or amino acid sequence this is to be understood to represent a corresponding sequence in which one or more nucleotides or amino acids have been added, deleted, substituted or otherwise chemically modified, provided always that the homologue retains substantially the same catalaytic properties as the particular sequence described. One particular type of homologue for example may be that in which one or more nucleotides have been substituted due to the degeneracy of the genetic code. Homologues, particularly longer versions of the sequences described herein, may be obtained by standard molecular biology and/or chemistry techniques, e.g. by cDNA or gene cloning, or by use of oligonucleotide directed mutagenesis or oligonucleotide directed synthesis techniques or enzymatic cleavage or enzymatic filling in of gapped oligonucleotides (see for example Ausubel, F. M. ibid).

The DNA of SEQ I.D. No: 1 and SEQ I.D. No: 2 each codes for part of a human metalloproteinase. Thus, the DNA according to the invention or a fragment thereof may be used as a probe to screen an appropriate genomic or cDNA library in a process utilising standard hybridisation and/or PCR cloning techniques to obtain the gene or cDNA coding for the entire metalloproteinase, or a homologue or fragment thereof, or a related metalloproteinase from another species.

Thus according to a further aspect of the invention we provide an isolated gene or cDNA coding for a human metalloproteinase, said gene or cDNA containing the nucleotide sequence of SEQ I.D. No: 1 or SEQ I.D. No: 2 or a homologue thereof.

The gene according to the invention may in turn be used to produce a metalloproteinase. In another aspect of the invention we therefore provide an isolated human metalloproteinase which contains the amino acid sequence of SEQ I.D. No: 3:

SEQ I.D. No: 3

FEHSKPTTRDWALQFTQQTKKRPRRMKREDLNSMKYVELYLVADYLEF
QKNRRDQDATKHKLIEIANYVDKFYRSLNIRIALVGLEVWTHGNMCEVSE
NPYSTLWSFLSWRRKLLAQKYHDNAQLITGMSFHGTTIGLAPMAMCSV
YQSGGVNMDHSENAIGVAATMAHEMGHNFGMTHDSADCCSASAADG
GCIMAAATGHPFPKVFNGCNRRELDRYLQSGGGMCLSNMPDTRMLYG
GRRCGNGYLEDGEECDCGEEEECNNPCCNASNCTLRPGAECAHGSCC
HQCKLLAPGTLCREQARQCDLPEFCTGKSPHCPTNFYQMDGTPCEGG
QAYCYNGMCLTYQEQCQQLWGPGARPAPDLCFEKVNAGDTFGNCG
KDMNGEHRKCNMRDAKCGKIQCQSSEARPLESNAVPIDTTIIMNGRQIQ
CRGTHVYRGPEEEGDMLDPGLVMTGTKCGYNHICFEGQCRNTSFFETE
GCGKKCNGHGVCNNNQNCHCLPGWAPPFCNTPGHGGSIDSGPMPPE
SVGPVVAGVLVAILVLAVLMLMYYCCRQNNKLGQLKPSALPSKLRQQFS
CPFRVSQNSGTGHANPTFKLQTPQGKRKVFLDCVQVINTPEILRKPSQ
PPPRPPPDYLRGGSPPAPLPAHLSRAARNSPGPGSQIERTESSRRPPPS
RIPPAPNCIVSQDFSRPRPPQKALPANPVPGRRSLPRPGGASPLRPPG
AGPQQSRPLAALAPKRVWKTCNLKTGDQFQSQ and homologues and fragments thereof.

The production of a protein according to the invention may be achieved using standard recombinant DNA techniques involving the expression of the metalloproteinase by a host cell. The isolated nucleic acids described herein may be for example introduced into any suitable expression vector by operatively linking the DNA to any necessary expression control elements therein and transforming any suitable procaryotic or eucaryotic host cell with the vector using well known procedures. The invention is thus to be understood to extend to recombinant plasmids containing a gene of the invention or a nucleotide sequence of SEQ I.D. No: 1 or SEQ I.D. No: 2, to cells containing said recombinant plasmids and to a process for producing the protein according to the invention which comprises culturing said cells such that the desired protein is expressed and recovering the protein from the culture.

Thus in one example the nucleotide sequence of SEQ I.D. No: 1, without its 3' poly A tail, or SEQ I.D. No: 2, or a homologue such as a longer version including a sequence encoding a signal peptide for secretion, and a propeptide to ensure accurate enzyme folding, is inserted downstream of the hCMV promoter in the pEE12 plasmid vector, and either transiently or stabily expressed in CHO-L761h or NSO mouse melanoma cells [Murphy et al., J. Biol. Chem., 267, 9612–9618 (1992)]. Expression of the enzyme according to the invention can be detected in serum free culture medium by its catalytic properties, or by Western blotting [Murphy et al., Biochem. J., 283, 637–641 (1992); Murphy et al., J. Biol. Chem., 267, 9612–9618 (1992)]. Such assays can also be used during the subsequent isolation of the expressed enzyme from transfected cell conditioned medium. If the enzyme requires further activation, this may be achieved proteolytically through use of modest amounts of trypsin, furin, or other methods, in order to remove an approximately 180 amino acid N-terminal propeptide, as described for other metalloproteinases [Murphy et al., J. Biol. Chem., 267, 9612–9618 (1992); Crabbe et al., Biochemistry, 33, 14419–14425 (1994); Pei and Weiss, Nature, 375, 244–247 (1995); Will et al., J. Biol. Chem., 271, 17119–17123 (1996)]

It may be desirable to produce the catalytic domain of the protein according to the invention in isolation from the rest of the molecule. This may be achieved using the above standard recombinant DNA techniques except that in this instance the DNA sequence used is that encoding the amino acid sequence of SEQ I.D. No: 4:

SEQ I.D. No: 4

MKREDLNSMKYVELYLVADYLEFQKNRRDQDATKHKLIEIANYVDKFYR
SLNIRIALVGLEVWTHGNMCEVSENPYSTLWSFLSWRRKLLAQKYHDNA
QLITGMSFHGTTIGLAPLMAMCSVYQSGGVNMDHSENAIGVAATMAHE
MGHNFGMTHDSADCCSASAADGGCIMAAATGHPFPKVFNGCNRRELD
RYLQSGGGMCLSNMPDTRMLYG or a homologue thereof, and the invention extends to such isolated catalytic domains.

N or C-terminally extended versions of the sequence shown in SEQ I.D. No: 4 may be obtained by expression in procaryotic or eucaryotic cells as described above optionally attached to a peptide tag via which the protein may be affinity purified and identified. Examples of tags include the well known "His" or "Strep-tags". Further sequences that may be attached arise from expression in procaryotic cells and include the peIB or ompA leaders which when placed at the N-terminus help direct secretion to the *E.coli* periplasmic space [Schmidt and Skerra, J. Chromatography, 676, 337–345 (1994); Knauper et al., J. Biol. Chem., 271, 17124–17131 (1996)].

The gene or nucleotide sequences according to the invention may also be of use in diagnosis, for example to determine enzyme deficiency in a human subject, by for example direct DNA sequence comparison or DNA/RNA hybridisation assays; or in therapy, for example where it is desired to modify the production of the metalloproteinase in vivo, and the invention extends to such uses.

Knowledge of the gene according to the invention also provides the ability to regulate its activity in vivo by for example the use of antisense DNA or RNA. Thus, according to a further aspect of the invention we provide an antisense DNA or an antisense RNA of a gene coding for a human metalloproteinase, said gene containing the nucleotide sequence of formulae SEQ I.D. No: 1 or SEQ I.D. No: 2.

The antisense DNA or RNA will correspond to the metalloproteinase gene or a fragment thereof, for example a fragment based on the nucleotide sequence of SEQ I.D. No: 1 or SEQ I.D. No: 2. The antisense DNA or RNA can be produced using conventional means, by standard molecular biology and/or by chemical synthesis as described above. If desired, the antisense DNA and antisense RNA may be chemically modified so as to prevent degradation in vivo or to facilitate passage through a cell membrane, and/or a substance capable of inactivating mRNA, for example ribosyme, may be linked thereto, and the invention extends to such constructs.

The antisense DNA or antisense RNA may be of use in the treatment of diseases or disorders in humans in which the over- or unregulated production of the metalloproteinase has been implicated. Such diseases or disorders may include those described under the general headings of infectious diseases, e.g. HIV infection; inflammatory disease/ autoimmunity e.g. rheumatoid arthritis, inflammatory bowel disease; osteoarthritis; cancer; allergic/atopic diseases e.g. asthma, eczema; cardiovascular disease e.g. myocardial infarction, congestive heart failure; systemic inflammatory response syndrome e.g. sepsis syndrome; reperfusion injury; malignancy; cachexia; congenital e.g. cystic fibrosis, sickle cell anaemia; dermatologic, e.g. psoriasis, alopecia; neurologic, e.g. multiple sclerosis, migraine headache; renal e.g. uraemia, nephrotic syndrome; obstetric/gynecologic e.g. premature labour, miscarriage, genitourinary prolapse, urinary incontinence, contraception, infertility; transplants e.g. organ transplant rejection, graft-versus-host disease; metabolic/idiopathic disease e.g. diabetes; disorders of the bone such as osteoporosis; and toxicity e.g. due to chemotherapy, cytokine therapy, and anti-CD3 therapy.

The metalloproteinase according to the invention and homologues or fragments thereof may be used to generate substances which selectively bind to the proteins and in so doing regulate the activity of the enzymes.

Such substances include, for example, antibodies, and the invention extends in particular to an antibody which is capable of recognising one or more epitopes on a metalloproteinase containing the amino acid sequence of SEQ I.D. No: 3, or a homologue or fragment thereof. In particular the antibody may be a neutralising antibody As used herein the term antibody is to be understood to mean a whole antibody or a fragment thereof, for example a F(ab)$_2$, Fab, Fv, $V_H$ or $V_K$ fragment, a single-chain antibody, a multimeric monospecific antibody or fragment thereof, or a bi- or multispecific antibody or fragment thereof.

The antibody according to the invention may be a polyclonal or, especially, a monoclonal antibody. The antibody may belong to any immunoglobulin class, and may be for example an IgG, for example IgG$_1$, IgG$_2$, IgG$_3$, IgG$_4$, IgE, IgM or IgA antibody. It may be of animal, for example mammalian origin, and may be for example a murine, rat or human antibody. Alternatively, the antibody may be a chimeric antibody. The term chimeric antibody is used herein to mean any antibody containing portions derived from different animal species. Particular examples include those antibodies having a variable region derived from a murine or other antibody constant region, and those antibodies in which one or more CDR sequences and optionally one or more variable region framework amino acids are derived from a murine or other antibody and the remaining portions of the variable and the constant regions are derived from a human immunoglobulin.

Antibodies according to the invention may be prepared by conventional immunisation and recombinant DNA techniques. Thus, for example polyclonal antibodies may be obtained from the sera of animals immunised with a metalloproteinase according to the invention or a homologue or fragment thereof. Any suitable host, for example BALB/c mice where it is desired to obtain a mouse polyclonal antibody, may be injected with the immunogen, the serum collected and the antibody recovered therefrom. Monoclonal antibodies may be obtained from hybridomas derived from the spleen cells of an animal immunised as just discussed and fused to an appropriate "immortal" B-tumour cell. In each instance, the antibody may be recovered from either the serum or the hybridoma by making use of standard purification and or concentration techniques, for example by chromatography, using for example Protein A or by other affinity chromatography employing a metalloproteinase of the invention or a homologue or fragment thereof.

Once a cell line, for example a hybridoma, expressing an antibody according to the invention has been obtained it is possible to clone therefrom the cDNA and to identify the variable region genes encoding the desired antibody, including the sequences encoding the CDRs. From here, other chimeric antibodies according to the invention may be obtained by preparing one or more replicable expression vectors containing at least the DNA sequence encoding the variable domain of the antibody heavy or light chain and optionally other DNA sequences encoding remaining portions of the heavy and/or light chains as desired, and transforming an appropriate cell line, e.g. a non-producing myeloma cell line, such as a mouse NSO line, in which production of the antibody will occur. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al [Molecular Cloning, Cold Spring Harbor Laboratory, New York, 1989]; DNA sequencing can be performed as described in Sanger et al [PNAS 74, 5463, (1977)] and the Amersham International plc sequencing handbook; and site directed mutagenesis can be carried out according to the method of Kramer et al [Nucl. Acids Res. 12, 9441, (1984)] and the Anglian Biotechnology Ltd handbook. Additionally, there are numerous publications, including patent specifications, detailing techniques suitable for the preparation of antibodies by manipulation of DNA, creation of expression vectors and transformation of appropriate cells, for example as reviewed by Mountain A. and Adair, J. R. in Biotechnology and Genetic Engineering Reviews [ed. Tombs, M. P., 10, Chapter 1, 1992, Intercept, Andover, UK] and in International Patent Specification No. WO 91/09967.

Antibodies and other selective binding agents according to the invention may be of use in therapy, either alone or as a delivery agent, for the delivery of a drug, prodrug, radiometal or radioisotope for example in the treatment of diseases such as those described above in humans and/or other animals, or may find a use as purification agents in the preparation of the human metalloproteinase or homologues or fragments thereof.

In a further use according to the invention, selective binding agents of the invention, such as antibodies, may form the basis of a diagnostic assay to detect the presence or absence in a biological sample (e.g. serum, synovial fluid or a tissue extract) of a metalloproteinase as described herein. Thus for example the binding agent may be brought into contact with a sample of serum, synovial fluid or tissue under conditions in which a complex is formed between the binding agent and target metalloproteinase. Qualitative and/or quantitative detection of the complex can then be used to determine the presence or absence of the metalloproteinase and in particular whether the enzyme is present in an abnormal quantity associated for example with a particular disease state.

The metalloproteinases according to the invention may in particular be used to screen for compounds which regulate the activity of the enzymes and the invention extends to such a screen and to the use of compounds obtainable therefrom to regulate metalloproteinases in vivo.

Thus according to a further aspect of the invention we provide a process for obtaining a compound capable of regulating the action of a human metalloproteinase in vivo which comprises subjecting one or more test compounds to a screen comprising (A) a metalloproteinase containing the amino acid sequence of SEQ I.D. No: 3 or a homologue or fragment thereof, or (B) a host cell transformed to be capable of expressing a metalloproteinase gene or cDNA or a homologue or fragment thereof containing a nucleotide sequence of SEQ I.D. No: 1 or SEQ I.D. No: 2 or a homologue or fragment thereof.

The screen according the invention may be operated using conventional procedures, for example by bringing the test compound or compounds to be screened and an appropriate substrate into contact with the metalloproteinase or a cell capable of producing it and determining affinity for the protein in accordance with standard practice.

Any compound obtainable in this way may have a potential use in the treatment in humans and/or other animals of one or more of the above mentioned diseases. The invention thus extends to a compound selected through its ability to regulate the activity of a metalloproteinase in vivo as primarily determined in a screening assay utilising a metalloproteinase containing an amino acid sequence of SEQ I.D. No: 3 or a homologue or fragment thereof or a gene coding therefor, for use in the treatment of a disease in which the over- or under-activity or unregulated activity of the metalloproteinase is implicated.

We claim:

1. Isolated human DNA comprising the nucleotide sequence of SEQ I.D. No: 1 herein and fragments thereof, wherein the protein encoded retains metalloproteinase activity.

2. Isolated DNA according to claim 1 having the human metalloproteinase-encoding nucleotide sequence of SEQ I.D. No: 2 herein and fragments thereof, wherein the protein encoded retains metalloproteinase activity.

3. An isolated gene or cDNA coding for a human metalloproteinase, said gene or cDNA containing the nucleotide sequence of SEQ ID. No: 1 or SEQ I.D. No: 2 herein.

4. An antisense DNA or an antisense RNA of a gene coding for a human metalloproteinase, said gene containing the nucleotide sequence of SEQ I.D. No: 1 or SEQ I.D. No: 2 herein.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2648 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GGTTCGAGCA   CTCCAAGCCC   ACCACCAGGG   ACTGGGCTCT   TCAGTTTACA   CAACAGACCA              6 0
```

| | | | | | |
|---|---|---|---|---|---|
| AGAAGCGACC | TCGCAGGATG | AAAAGGGAAG | ATTTAAACTC | CATGAAGTAT | GTGGAGCTTT | 120 |
| ACCTCGTGGC | TGATTATTTA | GAGTTTCAGA | AGAATCGACG | AGACCAGGAC | GCCACCAAAC | 180 |
| ACAAGCTCAT | AGAGATCGCC | AACTATGTTG | ATAAGTTTTA | CCGATCCTTG | AACATCCGGA | 240 |
| TTGCTCTCGT | GGGCTTGGAA | GTGTGGACCC | ACGGGAACAT | GTGTGAAGTT | TCAGAGAATC | 300 |
| CATATTCTAC | CCTCTGGTCC | TTTCTCAGTT | GGAGGCGCAA | GCTGCTTGCC | AGAAGTACC | 360 |
| ATGACAACGC | CCAATTAATC | ACGGGCATGT | CCTTCCACGG | CACCACCATC | GGCCTGGCCC | 420 |
| CCCTCATGGC | CATGTGCTCT | GTGTACCAGT | CTGGAGGAGT | CAACATGGAC | CACTCCGAGA | 480 |
| ATGCCATTGG | CGTGGCTGCC | ACCATGGCCC | ACGAGATGGG | CCACAACTTT | GGCATGACCC | 540 |
| ATGATTCTGC | AGATTGCTGC | TCGGCCAGTG | CGGCTGATGG | TGGGTGCATC | ATGGCAGCTG | 600 |
| CCACTGGGCA | CCCCTTTCCC | AAAGTGTTCA | ATGGATGCAA | CAGGAGGGAG | CTGGACAGGT | 660 |
| ATCTGCAGTC | AGGTGGTGGA | ATGTGTCTCT | CCAACATGCC | AGACACCAGG | ATGTTGTATG | 720 |
| GAGGCCGGAG | GTGTGGGAAC | GGGTATCTGG | AAGATGGGGA | AGAGTGTGAC | TGTGGAGAAG | 780 |
| AAGAGGAATG | TAACAACCCC | TGCTGCAATG | CCTCTAATTG | TACCCTGAGG | CCGGGGGCGG | 840 |
| AGTGTGCTCA | CGGCTCCTGC | TGCCACCAGT | GTAAGCTGTT | GGCTCCTGGG | ACCCTGTGCC | 900 |
| GCGAGCAGGC | CAGGCAGTGT | GACCTCCCGG | AGTTCTGTAC | GGGCAAGTCT | CCCCACTGCC | 960 |
| CTACCAACTT | CTACCAGATG | GATGGTACCC | CCTGTGAGGG | CGGCCAGGCC | TACTGCTACA | 1020 |
| ACGGCATGTG | CCTCACCTAC | CAGGAGCAGT | GCCAGCAGCT | GTGGGGACCC | GGAGCCCGAC | 1080 |
| CTGCCCCTGA | CCTCTGCTTC | GAGAAGGTGA | ATGTGGCAGG | AGACACCTTT | GGAAACTGTG | 1140 |
| GAAAGGACAT | GAATGGTGAA | CACAGGAAGT | GCAACATGAG | AGATGCGAAG | TGTGGGAAGA | 1200 |
| TCCAGTGTCA | GAGCTCTGAG | GCCCGGCCCC | TGGAGTCCAA | CGCGGTGCCC | ATTGACACCA | 1260 |
| CTATCATCAT | GAATGGGAGG | CAGATCCAGT | GCCGGGGCAC | CCACGTCTAC | CGAGGTCCTG | 1320 |
| AGGAGGAGGG | TGACATGCTG | GACCCAGGGC | TGGTGATGAC | TGGAACCAAG | TGTGGCTACA | 1380 |
| ACCATATTTG | CTTTGAGGGG | CAGTGCAGGA | ACACCTCCTT | CTTTGAAACT | GAAGGCTGTG | 1440 |
| GGAAGAAGTG | CAATGGCCAT | GGGGTCTGTA | ACAACAACCA | GAACTGCCAC | TGCCTGCCGG | 1500 |
| GCTGGGCCCC | GCCCTTCTGC | AACACACCGG | GCCACGGGGG | CAGTATCGAC | AGTGGGCCTA | 1560 |
| TGCCCCCTGA | GAGTGTGGGT | CCTGTGGTAG | CTGGAGTGTT | GGTGGCCATC | TTGGTGCTGG | 1620 |
| CGGTCCTCAT | GCTGATGTAC | TACTGCTGCA | GACAGAACAA | CAAACTAGGC | CAACTCAAGC | 1680 |
| CCTCAGCTCT | CCCTTCCAAG | CTGAGGCAAC | AGTTCAGTTG | TCCCTTCAGG | GTTTCTCAGA | 1740 |
| ACAGCGGGAC | TGGTCATGCC | AACCCAACTT | TCAAGCTGCA | GACGCCCCAG | GCAAGCGAA | 1800 |
| AGGTGTTCCT | TGACTTGTGC | GTACAGGTGA | TCAACACTCC | GGAAATCCTG | CGGAAGCCCT | 1860 |
| CCCAGCCTCC | TCCCCGGCCC | CCTCCAGATT | ATCTGCGTGG | TGGGTCCCCA | CCTGCACCAC | 1920 |
| TGCCAGCTCA | CCTGAGCAGG | GCTGCTAGGA | ACTCCCCAGG | GCCCGGGTCT | CAAATAGAGA | 1980 |
| GGACGGAGTC | GTCCAGGAGG | CCTCCTCCAA | GCCGGCCAAT | TCCCCCCGCA | CCAAATTGCA | 2040 |
| TCGTTTCCCA | GGACTTCTCC | AGGCCTCGGC | CGCCCCAGAA | GGCACTCCCG | GCAAACCCAG | 2100 |
| TGCCAGGCCG | CAGGAGCCTC | CCCAGGCCAG | GAGGTGCATC | CCCACTGCGG | CCCCCTGGTG | 2160 |
| CTGGCCCTCA | GCAGTCCCGG | CCTCTGGCAG | CACTTGCCCC | AAAGAGGGTA | TGGAAGACTT | 2220 |
| GCAATTTGAA | AACTGGGGAC | CAGTTCCAAA | GTCAGTAATT | GTGTTAACCA | CGTGTATAAC | 2280 |
| AGCTCTGCTG | GACACCCAAG | AAAGCCATGG | GAACGCCAAC | TGGAAAGGTC | CCCTTCCCCA | 2340 |
| GGGGAGCCTG | CGAAGGAGAG | GTTCTGTAGA | ATCCAAGCCC | ACATTTCCAA | AGTCACCCCC | 2400 |
| AACGCGTCCT | CTCACACCGT | CCACTGTGCG | TTTGTATGTG | TCTGGGATCC | AGGGCAATGT | 2460 |

```
GAATTTTCTT   TTTATTTGGG   AGATTGTTCA   CGGAAAACAG   ATCTTCTTCT   CTCTTGTCCA      2520

CCTATTAATT   GTTTACAATA   TTTGTACATC   TATGCAAAAT   ACTTGAATGG   GCCATGGTGC      2580

CTTTTTTCCT   TGTTAGTATT   TAATTAAAAA   TGAATTGTTT   GTCATTTGCA   AAAAAAAAA      2640

AAAAAAAA                                                                         2648
```

( 2 ) INFORMATION FOR SEQ ID NO:2:

( i ) SEQUENCE CHARACTERISTICS:
        ( A ) LENGTH: 2251 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
TTCGAGCACT   CCAAGCCCAC   CACCAGGGAC   TGGGCTCTTC   AGTTTACACA   ACAGACCAAG       60

AAGCGACCTC   GCAGGATGAA   AAGGGAAGAT   TTAAACTCCA   TGAAGTATGT   GGAGCTTTAC      120

CTCGTGGCTG   ATTATTTAGA   GTTTCAGAAG   AATCGACGAG   ACCAGGACGC   CACCAAACAC      180

AAGCTCATAG   AGATCGCCAA   CTATGTTGAT   AAGTTTTACC   GATCCTTGAA   CATCCGGATT      240

GCTCTCGTGG   GCTTGGAAGT   GTGGACCCAC   GGGAACATGT   GTGAAGTTTC   AGAGAATCCA      300

TATTCTACCC   TCTGGTCCTT   TCTCAGTTGG   AGGCGCAAGC   TGCTTGCCCA   GAAGTACCAT      360

GACAACGCCC   AATTAATCAC   GGGCATGTCC   TTCCACGGCA   CCACCATCGG   CCTGGCCCCC      420

CTCATGGCCA   TGTGCTCTGT   GTACCAGTCT   GGAGGAGTCA   ACATGGACCA   CTCCGAGAAT      480

GCCATTGGCG   TGGCTGCCAC   CATGGCCCAC   GAGATGGGCC   ACAACTTTGG   CATGACCCAT      540

GATTCTGCAG   ATTGCTGCTC   GGCCAGTGCG   GCTGATGGTG   GGTGCATCAT   GGCAGCTGCC      600

ACTGGGCACC   CCTTTCCCAA   AGTGTTCAAT   GGATGCAACA   GGAGGGAGCT   GGACAGGTAT      660

CTGCAGTCAG   GTGGTGGAAT   GTGTCTCTCC   AACATGCCAG   ACACCAGGAT   GTTGTATGGA      720

GGCCGGAGGT   GTGGGAACGG   GTATCTGGAA   GATGGGAAG   AGTGTGACTG   TGGAGAAGAA      780

GAGGAATGTA   ACAACCCCTG   CTGCAATGCC   TCTAATTGTA   CCCTGAGGCC   GGGGGCGGAG      840

TGTGCTCACG   GCTCCTGCTG   CCACCAGTGT   AAGCTGTTGG   CTCCTGGGAC   CCTGTGCCGC      900

GAGCAGGCCA   GGCAGTGTGA   CCTCCCGGAG   TTCTGTACGG   GCAAGTCTCC   CCACTGCCCT      960

ACCAACTTCT   ACCAGATGGA   TGGTACCCCC   TGTGAGGGCG   GCCAGGCCTA   CTGCTACAAC     1020

GGCATGTGCC   TCACCTACCA   GGAGCAGTGC   CAGCAGCTGT   GGGGACCCGG   AGCCCGACCT     1080

GCCCCTGACC   TCTGCTTCGA   GAAGGTGAAT   GTGGCAGGGA   CACCTTTGGA   AACTGTGGAA     1140

AGGACATGAA   TGGTGAACAC   AGGAAGTGCA   ACATGAGAGA   TGCGAAGTGT   GGGAAGATCC     1200

AGTGTCAGAG   CTCTGAGGCC   CGGCCCCTGG   AGTCCAACGC   GGTGCCCATT   GACACCACTA     1260

TCATCATGAA   TGGGAGGCAG   ATCCAGTGCC   GGGGCACCCA   CGTCTACCGA   GGTCCTGAGG     1320

AGGAGGGTGA   CATGCTGGAC   CCAGGGCTGG   TGATGACTGG   AACCAAGTGT   GGCTACAACC     1380

ATATTTGCTT   TGAGGGCAGT   GCAGGAACAC   CTCCTTCTTT   GAAACTGAAG   GCTGTGGGAA     1440

GAAGTGCAAT   GGCCATGGGG   TCTGTAACAA   CAACCAGAAC   TGCCACTGCC   TGCCGGGCTG     1500

GGCCCCGCCC   TTCTGCAACA   CACCGGGCCA   CGGGGGCAGT   ATCGACAGTG   GCCTATGCC     1560

CCCTGAGAGT   GTGGGTCCTG   TGGTAGCTGG   AGTGTTGGTG   GCCATCTTGG   TGCTGGCGGT     1620

CCTCATGCTG   ATGTACTACT   GCTGCAGACA   GAACAACAAA   CTAGGCCAAC   TCAAGCCCTC     1680

AGCTCTCCCT   TCCAAGCTGA   GGCAACAGTT   CAGTTGTCCC   TTCAGGGTTT   CTCAGAACAG     1740

CGGGACTGGT   CATGCCAACC   CAACTTTCAA   GCTGCAGACG   CCCCAGGGCA   AGCGAAAGGT     1800
```

| | | | | | | |
|---|---|---|---|---|---|---|
| GTTCCTTGAC | TTGTGCGTAC | AGGTGATCAA | CACTCCGGAA | ATCCTGCGGA | AGCCCTCCCA | 1860 |
| GCCTCCTCCC | CGGCCCCCTC | CAGATTATCT | GCGTGGTGGG | TCCCCACCTG | CACCACTGCC | 1920 |
| AGCTCACCTG | AGCAGGGCTG | CTAGGAACTC | CCCAGGGCCC | GGGTCTCAAA | TAGAGAGGAC | 1980 |
| GGAGTCGTCC | AGGAGGCCTC | CTCCAAGCCG | GCCAATTCCC | CCCGCACCAA | ATTGCATCGT | 2040 |
| TTCCCAGGAC | TTCTCCAGGC | CTCGGCCGCC | CCAGAAGGCA | CTCCCGGCAA | ACCCAGTGCC | 2100 |
| AGGCCGCAGG | AGCCTCCCCA | GGCCAGGAGG | TGCATCCCCA | CTGCGGCCCC | CTGGTGCTGG | 2160 |
| CCCTCAGCAG | TCCCGGCCTC | TGGCAGCACT | TGCCCCAAAG | AGGGTATGGA | AGACTTGCAA | 2220 |
| TTTGAAAACT | GGGGACCAGT | TCCAAAGTCA | G | | | 2251 |

( 2 ) INFORMATION FOR SEQ ID NO:3:

( i ) SEQUENCE CHARACTERISTICS:
        ( A ) LENGTH: 751 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:3:

```
Phe  Glu  His  Ser  Lys  Pro  Thr  Thr  Arg  Asp  Trp  Ala  Leu  Gln  Phe  Thr
 1                  5                  10                           15

Gln  Gln  Thr  Lys  Lys  Arg  Pro  Arg  Arg  Met  Lys  Arg  Glu  Asp  Leu  Asn
              20                       25                      30

Ser  Met  Lys  Tyr  Val  Glu  Leu  Tyr  Leu  Val  Ala  Asp  Tyr  Leu  Glu  Phe
                   35                  40                  45

Gln  Lys  Asn  Arg  Arg  Asp  Gln  Asp  Ala  Thr  Lys  His  Lys  Leu  Ile  Glu
              50                  55                       60

Ile  Ala  Asn  Tyr  Val  Asp  Lys  Phe  Tyr  Arg  Ser  Leu  Asn  Ile  Arg  Ile
 65                       70                       75                        80

Ala  Leu  Val  Gly  Leu  Glu  Val  Trp  Thr  His  Gly  Asn  Met  Cys  Glu  Val
                        85                       90                       95

Ser  Glu  Asn  Pro  Tyr  Ser  Thr  Leu  Trp  Ser  Phe  Leu  Ser  Trp  Arg  Arg
                   100                      105                      110

Lys  Leu  Leu  Ala  Gln  Lys  Tyr  His  Asp  Asn  Ala  Gln  Leu  Ile  Thr  Gly
                   115                      120                      125

Met  Ser  Phe  His  Gly  Thr  Thr  Ile  Gly  Leu  Ala  Pro  Leu  Met  Ala  Met
      130                      135                      140

Cys  Ser  Val  Tyr  Gln  Ser  Gly  Gly  Val  Asn  Met  Asp  His  Ser  Glu  Asn
 145                      150                      155                      160

Ala  Ile  Gly  Val  Ala  Ala  Thr  Met  Ala  His  Glu  Met  Gly  His  Asn  Phe
                        165                      170                      175

Gly  Met  Thr  His  Asp  Ser  Ala  Asp  Cys  Cys  Ser  Ala  Ser  Ala  Ala  Asp
                   180                      185                      190

Gly  Gly  Cys  Ile  Met  Ala  Ala  Ala  Thr  Gly  His  Pro  Phe  Pro  Lys  Val
           195                      200                      205

Phe  Asn  Gly  Cys  Asn  Arg  Arg  Glu  Leu  Asp  Arg  Tyr  Leu  Gln  Ser  Gly
      210                      215                      220

Gly  Gly  Met  Cys  Leu  Ser  Asn  Met  Pro  Asp  Thr  Arg  Met  Leu  Tyr  Gly
 225                      230                      235                      240

Gly  Arg  Arg  Cys  Gly  Asn  Gly  Tyr  Leu  Glu  Asp  Gly  Glu  Glu  Cys  Asp
                   245                      250                      255

Cys  Gly  Glu  Glu  Glu  Glu  Cys  Asn  Asn  Pro  Cys  Cys  Asn  Ala  Ser  Asn
                   260                      265                      270
```

```
Cys Thr Leu Arg Pro Gly Ala Glu Cys Ala His Gly Ser Cys Cys His
        275                 280                 285
Gln Cys Lys Leu Leu Ala Pro Gly Thr Leu Cys Arg Glu Gln Ala Arg
        290                 295                 300
Gln Cys Asp Leu Pro Glu Phe Cys Thr Gly Lys Ser Pro His Cys Pro
305                 310                 315                 320
Thr Asn Phe Tyr Gln Met Asp Gly Thr Pro Cys Glu Gly Gly Gln Ala
                325                 330                 335
Tyr Cys Tyr Asn Gly Met Cys Leu Thr Tyr Gln Glu Gln Cys Gln Gln
                340                 345                 350
Leu Trp Gly Pro Gly Ala Arg Pro Ala Pro Asp Leu Cys Phe Glu Lys
        355                 360                 365
Val Asn Val Ala Gly Asp Thr Phe Gly Asn Cys Gly Lys Asp Met Asn
370                 375                 380
Gly Glu His Arg Lys Cys Asn Met Arg Asp Ala Lys Cys Gly Lys Ile
385                 390                 395                 400
Gln Cys Gln Ser Ser Glu Ala Arg Pro Leu Glu Ser Asn Ala Val Pro
                405                 410                 415
Ile Asp Thr Thr Ile Ile Met Asn Gly Arg Gln Ile Gln Cys Arg Gly
            420                 425                 430
Thr His Val Tyr Arg Gly Pro Glu Glu Glu Gly Asp Met Leu Asp Pro
        435                 440                 445
Gly Leu Val Met Thr Gly Thr Lys Cys Gly Tyr Asn His Ile Cys Phe
450                 455                 460
Glu Gly Gln Cys Arg Asn Thr Ser Phe Phe Glu Thr Glu Gly Cys Gly
465                 470                 475                 480
Lys Lys Cys Asn Gly His Gly Val Cys Asn Asn Gln Asn Cys His
                485                 490                 495
Cys Leu Pro Gly Trp Ala Pro Pro Phe Cys Asn Thr Pro Gly His Gly
            500                 505                 510
Gly Ser Ile Asp Ser Gly Pro Met Pro Pro Glu Ser Val Gly Pro Val
        515                 520                 525
Val Ala Gly Val Leu Val Ala Ile Leu Val Leu Ala Val Leu Met Leu
    530                 535                 540
Met Tyr Tyr Cys Cys Arg Gln Asn Asn Lys Leu Gly Gln Leu Lys Pro
545                 550                 555                 560
Ser Ala Leu Pro Ser Lys Leu Arg Gln Gln Phe Ser Cys Pro Phe Arg
                565                 570                 575
Val Ser Gln Asn Ser Gly Thr Gly His Ala Asn Pro Thr Phe Lys Leu
            580                 585                 590
Gln Thr Pro Gln Gly Lys Arg Lys Val Phe Leu Asp Leu Cys Val Gln
        595                 600                 605
Val Ile Asn Thr Pro Glu Ile Leu Arg Lys Pro Ser Gln Pro Pro Pro
    610                 615                 620
Arg Pro Pro Pro Asp Tyr Leu Arg Gly Gly Ser Pro Pro Ala Pro Leu
625                 630                 635                 640
Pro Ala His Leu Ser Arg Ala Ala Arg Asn Ser Pro Gly Pro Gly Ser
                645                 650                 655
Gln Ile Glu Arg Thr Glu Ser Ser Arg Arg Pro Pro Ser Arg Pro
            660                 665                 670
Ile Pro Pro Ala Pro Asn Cys Ile Val Ser Gln Asp Phe Ser Arg Pro
        675                 680                 685
Arg Pro Pro Gln Lys Ala Leu Pro Ala Asn Pro Val Pro Gly Arg Arg
690                 695                 700
```

| Ser | Leu | Pro | Arg | Pro | Gly | Gly | Ala | Ser | Pro | Leu | Arg | Pro | Pro | Gly | Ala |
|-----|-----|-----|-----|-----|-----|-----|-----|-----|-----|-----|-----|-----|-----|-----|-----|
| 705 |     |     |     |     | 710 |     |     |     |     | 715 |     |     |     |     | 720 |

| Gly | Pro | Gln | Gln | Ser | Arg | Pro | Leu | Ala | Ala | Leu | Ala | Pro | Lys | Arg | Val |
|-----|-----|-----|-----|-----|-----|-----|-----|-----|-----|-----|-----|-----|-----|-----|-----|
|     |     |     |     | 725 |     |     |     |     | 730 |     |     |     |     | 735 |     |

| Trp | Lys | Thr | Cys | Asn | Leu | Lys | Thr | Gly | Asp | Gln | Phe | Gln | Ser | Gln |
|-----|-----|-----|-----|-----|-----|-----|-----|-----|-----|-----|-----|-----|-----|-----|
|     |     |     | 740 |     |     |     |     | 745 |     |     |     |     | 750 |     |

(2) INFORMATION FOR SEQ ID NO:4:

(i) SEQUENCE CHARACTERISTICS:
        (A) LENGTH: 215 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:4:

| Met | Lys | Arg | Glu | Asp | Leu | Asn | Ser | Met | Lys | Tyr | Val | Glu | Leu | Tyr | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Ala | Asp | Tyr | Leu | Glu | Phe | Gln | Lys | Asn | Arg | Arg | Asp | Gln | Asp | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Thr | Lys | His | Lys | Leu | Ile | Glu | Ile | Ala | Asn | Tyr | Val | Asp | Lys | Phe | Tyr |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Arg | Ser | Leu | Asn | Ile | Arg | Ile | Ala | Leu | Val | Gly | Leu | Glu | Val | Trp | Thr |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| His | Gly | Asn | Met | Cys | Glu | Val | Ser | Glu | Asn | Pro | Tyr | Ser | Thr | Leu | Trp |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ser | Phe | Leu | Ser | Trp | Arg | Arg | Lys | Leu | Leu | Ala | Gln | Lys | Tyr | His | Asp |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Asn | Ala | Gln | Leu | Ile | Thr | Gly | Met | Ser | Phe | His | Gly | Thr | Thr | Ile | Gly |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Leu | Ala | Pro | Leu | Met | Ala | Met | Cys | Ser | Val | Tyr | Gln | Ser | Gly | Gly | Val |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Asn | Met | Asp | His | Ser | Glu | Asn | Ala | Ile | Gly | Val | Ala | Ala | Thr | Met | Ala |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| His | Glu | Met | Gly | His | Asn | Phe | Gly | Met | Thr | His | Asp | Ser | Ala | Asp | Cys |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Cys | Ser | Ala | Ser | Ala | Ala | Asp | Gly | Gly | Cys | Ile | Met | Ala | Ala | Ala | Thr |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Gly | His | Pro | Phe | Pro | Lys | Val | Phe | Asn | Gly | Cys | Asn | Arg | Arg | Glu | Leu |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Asp | Arg | Tyr | Leu | Gln | Ser | Gly | Gly | Gly | Met | Cys | Leu | Ser | Asn | Met | Pro |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Asp | Thr | Arg | Met | Leu | Tyr | Gly |
|-----|-----|-----|-----|-----|-----|-----|
|     | 210 |     |     |     |     | 215 |